(12) United States Patent
Hadba et al.

(10) Patent No.: US 9,707,252 B2
(45) Date of Patent: Jul. 18, 2017

(54) SYNTHETIC SEALANTS

(75) Inventors: Ahmad R. Hadba, Wallingford, CT (US); John Kennedy, Guilford, CT (US); Mark Roby, Killingworth, CT (US)

(73) Assignee: Covidien LP, Mansfield, MA (US)

( * ) Notice: Subject to any disclaimer, the term of this patent is extended or adjusted under 35 U.S.C. 154(b) by 2294 days.

(21) Appl. No.: 11/883,993

(22) PCT Filed: Feb. 9, 2006

(86) PCT No.: PCT/US2006/004500
§ 371 (c)(1),
(2), (4) Date: Jun. 4, 2008

(87) PCT Pub. No.: WO2006/086510
PCT Pub. Date: Aug. 17, 2006

(65) Prior Publication Data
US 2009/0030451 A1    Jan. 29, 2009

Related U.S. Application Data

(60) Provisional application No. 60/651,389, filed on Feb. 9, 2005.

(51) Int. Cl.
| | |
|---|---|
| C08L 15/00 | (2006.01) |
| A61K 8/72 | (2006.01) |
| A61K 31/77 | (2006.01) |
| A61L 24/04 | (2006.01) |
| C08G 18/50 | (2006.01) |

(52) U.S. Cl.
CPC ............ *A61K 31/77* (2013.01); *A61L 24/043* (2013.01); *C08G 18/5024* (2013.01); *C08G 18/5039* (2013.01); *C08G 2190/00* (2013.01)

(58) Field of Classification Search
CPC ... A61K 31/77; A61L 24/043; C08G 18/5024; C08G 18/5039; C08G 2190/00
USPC ................................................. 523/111, 105
See application file for complete search history.

(56) References Cited

U.S. PATENT DOCUMENTS

| | | | |
|---|---|---|---|
| 3,520,949 A | 7/1970 | Shepard et al. | |
| 3,654,370 A * | 4/1972 | Yeakey | 564/480 |
| 3,773,595 A | 11/1973 | Burba et al. | |
| 3,939,123 A | 2/1976 | Matthews et al. | |
| 4,057,535 A | 11/1977 | Lipatova et al. | |
| 4,061,662 A | 12/1977 | Marans et al. | |
| 4,101,380 A | 7/1978 | Rubinstein et al. | |
| 4,169,175 A | 9/1979 | Marans et al. | |
| 4,323,491 A | 4/1982 | Veselovsky et al. | |
| 4,359,049 A | 11/1982 | Redl et al. | |
| 4,362,567 A | 12/1982 | Schwarz et al. | |
| 4,414,976 A | 11/1983 | Schwarz et al. | |
| 4,425,472 A | 1/1984 | Howard et al. | |
| 4,629,779 A | 12/1986 | Koleske | |
| 4,631,055 A | 12/1986 | Redl et al. | |
| 4,650,817 A | 3/1987 | Allen, Jr. et al. | |
| 4,741,872 A | 5/1988 | DeLuca et al. | |
| 4,804,691 A | 2/1989 | English et al. | |
| 4,822,841 A * | 4/1989 | Murray et al. | 524/356 |
| 4,826,945 A | 5/1989 | Cohn et al. | |
| 4,853,456 A | 8/1989 | Sellstrom et al. | |
| 4,874,368 A | 10/1989 | Miller et al. | |
| 4,938,763 A | 7/1990 | Dunn et al. | |
| 4,978,336 A | 12/1990 | Capozzi et al. | |
| 5,030,215 A | 7/1991 | Morse et al. | |
| 5,041,292 A | 8/1991 | Feijen | |
| 5,041,517 A | 8/1991 | Vu et al. | |
| 5,100,992 A | 3/1992 | Cohn et al. | |
| 5,104,909 A | 4/1992 | Grasel | |
| 5,116,315 A | 5/1992 | Capozzi et al. | |
| 5,143,662 A | 9/1992 | Chesterfield et al. | |
| 5,160,745 A | 11/1992 | DeLuca et al. | |
| 5,162,430 A | 11/1992 | Rhee et al. | |
| 5,166,300 A | 11/1992 | Rumon et al. | |
| 5,169,720 A | 12/1992 | Braatz et al. | |
| 5,175,228 A | 12/1992 | Wang et al. | |
| 5,192,743 A | 3/1993 | Hsu et al. | |
| 5,219,564 A | 6/1993 | Zalipsky et al. | |
| 5,239,048 A * | 8/1993 | Speranza et al. | 528/340 |
| 5,292,362 A | 3/1994 | Bass et al. | |
| 5,296,518 A | 3/1994 | Grasel | |
| 5,304,595 A | 4/1994 | Rhee et al. | |
| 5,318,524 A | 6/1994 | Morse et al. | |
| 5,320,886 A | 6/1994 | Bowen | |
| 5,324,775 A | 6/1994 | Rhee et al. | |
| 5,328,955 A | 7/1994 | Rhee et al. | |

(Continued)

FOREIGN PATENT DOCUMENTS

| | | |
|---|---|---|
| EP | 0 077 192 A2 | 4/1983 |
| EP | 0 482 467 | 4/1992 |
| EP | 0 488 629 | 6/1992 |
| EP | 0 301 516 | 9/1992 |
| EP | 0557199 | 8/1993 |
| EP | 1 391 205 A1 | 2/2005 |
| EP | 1 719 530 A | 11/2006 |
| EP | 1 719 530 A2 | 11/2006 |

(Continued)

OTHER PUBLICATIONS

US 6,214,374, 04/2001, Schmirler et al. (withdrawn)
International Search Report from PCT/US06/47013 dated Oct. 3, 2007.
International Search Report from PCT/US06/46558 dated Nov. 9, 2007.
International Search Report from PCT/US06/46552 dated Nov. 15, 2007.
International Search Report from PCT/US06/47023 dated Nov. 21, 2007.

(Continued)

*Primary Examiner* — David Karst

(57) ABSTRACT

A biocompatible synthetic macromer composition is provided which includes a first polymer having stiffening linkages and at least one amine group, and a second component having at least one amine-reactive group. The biocompatible synthetic macromer composition can be used as an adhesive or sealant in human and/or animal medical applications.

16 Claims, No Drawings

(56) References Cited

U.S. PATENT DOCUMENTS

| | | |
|---|---|---|
| 5,405,607 A | 4/1995 | Epstein |
| 5,410,016 A | 4/1995 | Hubbell et al. |
| 5,413,791 A | 5/1995 | Rhee et al. |
| 5,419,491 A | 5/1995 | Breitsprecher |
| 5,426,148 A | 6/1995 | Tucker |
| 5,446,090 A | 8/1995 | Harris |
| 5,446,091 A | 8/1995 | Rhee et al. |
| 5,455,027 A | 10/1995 | Zalipsky et al. |
| 5,462,536 A | 10/1995 | Braatz et al. |
| 5,470,911 A | 11/1995 | Rhee et al. |
| 5,474,540 A | 12/1995 | Miller et al. |
| 5,475,052 A | 12/1995 | Rhee et al. |
| 5,476,909 A | 12/1995 | Kim et al. |
| 5,505,704 A | 4/1996 | Pawelka et al. |
| 5,514,379 A | 5/1996 | Weissleder et al. |
| 5,514,380 A | 5/1996 | Song et al. |
| 5,527,856 A | 6/1996 | Rhee et al. |
| 5,529,914 A | 6/1996 | Hubbell et al. |
| 5,543,441 A | 8/1996 | Rhee et al. |
| 5,550,187 A | 8/1996 | Rhee et al. |
| 5,563,233 A | 10/1996 | Reich et al. |
| 5,565,519 A | 10/1996 | Rhee et al. |
| 5,567,435 A | 10/1996 | Hubbell et al. |
| 5,573,934 A | 11/1996 | Hubbell et al. |
| 5,578,310 A | 11/1996 | M'Timkulu et al. |
| 5,582,596 A | 12/1996 | Fukunaga et al. |
| 5,583,114 A | 12/1996 | Barrows et al. |
| 5,605,541 A | 2/1997 | Holm |
| 5,614,587 A | 3/1997 | Rhee et al. |
| 5,626,863 A | 5/1997 | Hubbell et al. |
| 5,631,322 A | 5/1997 | Veronese et al. |
| 5,643,464 A | 7/1997 | Rhee et al. |
| 5,686,089 A | 11/1997 | Mitra et al. |
| 5,702,361 A | 12/1997 | Evans et al. |
| 5,717,030 A | 2/1998 | Dunn et al. |
| 5,728,762 A | 3/1998 | Reich et al. |
| 5,741,223 A | 4/1998 | Janzen et al. |
| 5,741,551 A | 4/1998 | Guire et al. |
| 5,744,545 A | 4/1998 | Rhee et al. |
| 5,749,968 A | 5/1998 | Melanson et al. |
| 5,752,974 A | 5/1998 | Rhee et al. |
| 5,773,025 A | 6/1998 | Baichwal |
| 5,786,421 A | 7/1998 | Rhee et al. |
| 5,800,541 A | 9/1998 | Rhee et al. |
| 5,807,581 A | 9/1998 | Rosenblatt et al. |
| 5,844,023 A | 12/1998 | Tomka |
| 5,874,500 A | 2/1999 | Rhee et al. |
| 5,932,200 A | 8/1999 | Reich et al. |
| 5,932,462 A | 8/1999 | Harris et al. |
| 5,936,035 A | 8/1999 | Rhee et al. |
| 5,951,583 A | 9/1999 | Jensen et al. |
| 5,990,237 A | 11/1999 | Bentley et al. |
| 6,007,833 A | 12/1999 | Chudzik et al. |
| 6,033,654 A | 3/2000 | Stredronsky et al. |
| 6,046,305 A * | 4/2000 | Choi .................. 528/491 |
| 6,051,248 A | 4/2000 | Sawhney et al. |
| 6,051,648 A | 4/2000 | Rhee et al. |
| 6,071,530 A | 6/2000 | Polson |
| 6,083,524 A | 7/2000 | Sawhney et al. |
| 6,110,484 A | 8/2000 | Sierra |
| 6,124,273 A | 9/2000 | Drohan et al. |
| 6,140,452 A | 10/2000 | Felt et al. |
| 6,150,505 A | 11/2000 | Marx et al. |
| 6,152,943 A | 11/2000 | Sawhney |
| 6,156,531 A | 12/2000 | Pathak et al. |
| 6,162,241 A | 12/2000 | Coury et al. |
| 6,177,095 B1 | 1/2001 | Sawhney et al. |
| 6,179,862 B1 | 1/2001 | Sawhney |
| 6,183,498 B1 | 2/2001 | Devore et al. |
| 6,201,065 B1 | 3/2001 | Pathak et al. |
| 6,214,966 B1 | 4/2001 | Harris |
| 6,251,382 B1 | 6/2001 | Greenwald et al. |
| 6,258,351 B1 | 7/2001 | Harris |
| 6,261,544 B1 | 7/2001 | Coury et al. |
| 6,312,725 B1 | 11/2001 | Wallace et al. |
| 6,371,975 B2 | 4/2002 | Cruise et al. |
| 6,395,112 B1 | 5/2002 | Sitzmann et al. |
| 6,395,823 B1 | 5/2002 | Brink et al. |
| 6,458,889 B1 | 10/2002 | Trollsas et al. |
| 6,465,001 B1 | 10/2002 | Hubbell et al. |
| 6,495,127 B1 | 12/2002 | Wallace et al. |
| 6,503,731 B2 | 1/2003 | Marx et al. |
| 6,566,406 B1 | 5/2003 | Pathak et al. |
| 6,582,713 B2 | 6/2003 | Newell et al. |
| 6,656,200 B2 | 12/2003 | Li et al. |
| 6,673,093 B1 | 1/2004 | Sawhney |
| 7,009,034 B2 | 3/2006 | Pathak et al. |
| 2002/0015689 A1 | 2/2002 | Munro et al. |
| 2002/0026005 A1 | 2/2002 | Munro et al. |
| 2002/0028241 A1 | 3/2002 | Foreman et al. |
| 2002/0045706 A1 | 4/2002 | Houston et al. |
| 2003/0032734 A1 * | 2/2003 | Roby .................. 525/403 |
| 2004/0023842 A1 * | 2/2004 | Pathak et al. .......... 514/1 |
| 2004/0068078 A1 | 4/2004 | Milbocker |
| 2004/0076602 A1 | 4/2004 | Harris |
| 2004/0092695 A1 | 5/2004 | Hu et al. |
| 2004/0198901 A1 | 10/2004 | Graham et al. |
| 2005/0004661 A1 | 1/2005 | Lewis et al. |
| 2005/0069573 A1 | 3/2005 | Cohn et al. |
| 2005/0070913 A1 | 3/2005 | Milbocker et al. |
| 2005/0129733 A1 | 6/2005 | Milbocker et al. |
| 2005/0142162 A1 | 6/2005 | Hunter et al. |
| 2005/0147647 A1 | 7/2005 | Glauser et al. |
| 2005/0266086 A1 | 12/2005 | Sawhney |

FOREIGN PATENT DOCUMENTS

| | | |
|---|---|---|
| EP | 1857489 A1 | 11/2007 |
| GB | 985 144 | 3/1965 |
| JP | 6263850 | 9/1994 |
| JP | 2002060341 | 2/2002 |
| WO | WO 89/00589 A1 | 1/1989 |
| WO | WO 91/09641 | 7/1991 |
| WO | WO 94/03155 | 2/1994 |
| WO | WO 94/13311 | 6/1994 |
| WO | WO 96/03159 | 2/1996 |
| WO | WO 97/22371 | 6/1997 |
| WO | WO 98/35631 | 8/1998 |
| WO | 99/02168 A1 | 1/1999 |
| WO | WO 99/10022 | 3/1999 |
| WO | WO 99/14259 | 3/1999 |
| WO | WO 99/22770 | 5/1999 |
| WO | WO 99/34833 | 7/1999 |
| WO | WO 00/12018 | 3/2000 |
| WO | WO 00/72852 | 12/2000 |
| WO | WO 01/00246 A | 1/2001 |
| WO | WO 01/16210 A | 3/2001 |
| WO | WO 02/056790 A2 | 7/2002 |
| WO | WO 2004/039323 | 5/2004 |
| WO | WO 2005/032461 A2 | 4/2005 |
| WO | WO 2005/100429 A1 | 10/2005 |
| WO | WO 2006/010278 A1 | 2/2006 |
| WO | WO 2006/084911 A2 | 8/2006 |
| WO | WO 2006/107957 A2 | 10/2006 |
| WO | WO 2006/128742 A2 | 12/2006 |
| WO | WO 2006/128918 A1 | 12/2006 |
| WO | WO 2007/001448 A2 | 1/2007 |
| WO | WO 2007/067623 A | 6/2007 |
| WO | WO 2008/047100 A1 | 4/2008 |

OTHER PUBLICATIONS

International Search Report (Dated Mar. 20, 2007).
European Search Report for Appln. No. EP 08 25 3647 completed Mar. 6, 2009.
European Search Report for Appln. No. EP 08 25 1790.5 completed Jun. 19, 2009.
International Search Report from European Application No. EP 06 84 4894 date of completion Jun. 9, 2010.
International Search Report from European Application No. EP 06 84 4890 date of completion Jun. 4, 2010.

(56) References Cited

OTHER PUBLICATIONS

Margolin A L et al.: "Steroselective Oligomerizations Catalyzed by Lipases in Organic Olvents"; Tetrahedron Letters, vol. 28, No. 15, 1987pp. 1607-1610.

Okumura S. et al.: "Synthesis of Ester Oligomer by Aspergillus-Niger Lipase" Agricultural and Biological Chemistry, vol. 48, No. 11, 1984, pp. 2805-2808.

Lumann N R et al.: The convergent Synthesis of Poly(glycerol-succininc acid) Dendritic Marcomolecules: Chemistry—A European Journal, VCH Publishers, US vol. 9, 2003, pp. 5618-5626.

Nivasu V M et al.: "In Situ Polymerizable Polyethyleneglycol Containing Polyesterpolyol Acrylates for Tissue Sealant Applications"; Biomaterials 2004 United Kingdom, vol. 25, No. 16, 2004, pp. 3283-3291.

Moon S-Y et al.: Polyurethane/Montorillonite Nancomposites Prepared From Crystalline Polyols, Using 1, 4-Butanediol and Organoclay Hybrids as Chain Extenders: European Polymer Journal, Pergamon Press Ltd. Oxford, GB,; vol. 40, No. 8, Aug. 2004; pp. 1615-16213.

M. J. Song, D.S. Lee, J.H. Ahn, D.J. Kim, S.C. Kim: "Thermosensitive Sol-Gel Transition Behaviors of Poly(ethylene oide)/ Aliphatic Polyester/Poly(ethylene Oxide) Aqueous Solutions"; Journal of Polymer Science Part A: Polymer Chemistry, vol. 42, No. 3.; Feb. 1, 2004; pp. 772-784.

Mei Xuan Xu et al.: Synthesis and Properties of Unsaturated Polyester Dio-Polyurethanehybrid Polymer Network: Journal of Applied Polymer Science, John Wiley and Sons Inc. New York, US, vol. 54, No. 11, Dec. 12, 1994, pp. 1659-1663.

Oprea S. et al.: "Poly(urethane-methacrylates)s. Synthesis adn Characterization"; Polymer, Elsevier Science Publishers B.V., GB, vol. 42, No. 17, Aug. 2001, pp. 7257-7266.

deGroot, J.H. et al., Chapter 2: Preparation of Porous Biodegradable Polyurethanes for the Reconstruction of Meniscal Lesions, Colloid Polymer Science, 1990, 268: 1073-1081.

International Search Report from Application EP 07 00 1213 dated Sep. 6, 2007.

International Search Report from Application EP 03 77 9244 dated Sep. 26, 2007.

International Search Report from Application PCT/US2006/46553 dated Oct. 31, 2007.

International Search Report from Application PCT/US2006/46554 dated Oct. 31, 2007.

Database WPI, Section Ch, Week 199442 Derwent Publications Ltd. London, GB; Class A23, AN 1994-3383493 XP002394015 dated Sep. 20, 1994.

European Search Report EP 06 00 9170 dated Aug. 24, 2006.

Supplementary European Search Report from Application No. EP 06839253.9-2115 dated Jul. 16, 2012.

International Search Report from EP Application No. 13170126.0 dated Jul. 4, 2013.

* cited by examiner

SYNTHETIC SEALANTS

CROSS-REFERENCE TO RELATED APPLICATIONS

This application is a National State Application of PCT/US2006/004500 filed Feb. 9, 2006 under 35USC §371 (a), which claims priority of U.S. Provisional Patent Application Ser. No. 60/651,389 filed Feb. 9, 2005, the disclosures of each of the above-identified applications are hereby incorporated by reference in their entirety.

BACKGROUND

Technical Field

The present disclosure relates to crosslinked compositions made from synthetic polymers and the use of such compositions as biological adhesives and/or sealants.

Background of Related Art

In recent years there has developed increased interest in replacing or augmenting sutures with adhesive bonds. The reasons for this increased interest include: (1) the potential speed with which repair might be accomplished; (2) the ability of a bonding substance to effect complete closure, thus preventing seepage of fluids; and (3) the possibility of forming a bond without excessive deformation of tissue.

Studies in this area, however, have revealed that, in order for surgical adhesives to be accepted by surgeons, they should possess a number of properties. They should exhibit high initial tack and an ability to bond rapidly to living tissue; the strength of the bond should be sufficiently high to cause tissue failure before bond failure; the adhesive should form a bridge, preferably a permeable flexible bridge; and the adhesive bridge and/or its metabolic products should not cause local histotoxic or carcinogenic effects.

Several materials useful as a tissue adhesive or tissue sealant are currently available. One type of adhesive that is currently available is a cyanoacrylate adhesive. However, there is the possibility that a cyanoacrylate adhesive can degrade to generate undesirable by-products such as formaldehyde. Another disadvantage is that cyanoacrylate adhesives can have a high flexural modulus which can limit the usefulness of the adhesive.

Another type of tissue sealant that is currently available utilizes components derived from bovine and/or human sources. For example, fibrin sealants are available. However, as with any natural material, variability in the material is frequently observed and, because the sealant is derived from natural proteins, there may be viral transmission concerns.

It would be desirable to provide a biological adhesive that is fully synthetic and therefore highly consistent in its properties without the concern of viral transmission. Such an adhesive should be flexible and biocompatible and should be suitable for use as either an adhesive or sealant.

SUMMARY

Biocompatible synthetic macromer compositions useful as tissue adhesives or sealants of the present disclosure include a first polymer that is endcapped with amine groups and a second component that is terminated with an amine-reactive group such as, for example, a succinimidyl or isocyanate group. Either the first polymer, the second component, or both, may have stiffening linkages incorporated therein.

In another aspect, methods for adhering and/or forming a seal between two tissue surfaces in an animal are described. The methods include the steps of approximating a first tissue surface with a second tissue surface and applying the macromer composition of the present disclosure in contact with both the first and second tissue surfaces.

In an alternative embodiment, the present macromer compositions are used to secure a medical device (for example, an implant) to tissue. The medical device may be approximated with a first animal tissue surface and the disclosed macromer composition may be applied in contact with both the device and the tissue surface.

In another aspect, the present macromer compositions can be used as sealants or void fillers to fill a defect within animal tissue. The macromer composition can also be used as a sealant for air and/or fluid leaks, and can be suitable for use with delicate tissues where sutures, clamps or other conventional tissue closure mechanisms may cause further tissue damage.

DETAILED DESCRIPTION OF PREFERRED EMBODIMENTS

The biocompatible synthetic macromer compositions described herein may be useful as adhesives for adhering animal tissue or as sealants for sealing voids in animal tissue and may be made using at least two components; a first polymer with terminal amine groups, and a second component having amine-reactive groups. Either the first polymer component, the second component, or both, may have stiffening linkages. It is contemplated that the macromer compositions described herein may be utilized both as adhesives and/or sealants that can be applied to living tissue and/or flesh of animals, including humans.

While certain distinctions may be drawn between the usage of the terms "flesh" and "tissue" within the scientific community, the terms are used interchangeably herein as referring to a general substrate upon which those skilled in the art would understand the present adhesive to be utilized within the medical field for the treatment of patients. As used herein, "tissue" may include, but is not limited to, skin, bone, neuron, axon, cartilage, blood vessel, cornea, muscle, fascia, brain, prostate, breast, endometrium, lung, pancreas, small intestine, blood, liver, testes, ovaries, cervix, colon, stomach, esophagus, spleen, lymph node, bone marrow, kidney, peripheral blood, embryonic or ascite tissue.

In one embodiment, the first component of the biocompatible synthetic macromer composition of the present disclosure can have the formula:

$$H_2N-[R_1-Q-R_2]-NH_2 \qquad (I)$$

where $R_1$ and $R_2$ are the same or different and can be alkoxy, alkoxy with bioabsorbable groups such as esters, aliphatic esters, carbonates, orthoesters, phosphoesters, glycolic acid, glycolide, lactic acid, lactide, 1,4-dioxane-2-one, 1,3-dioxane-2-one, ε-caprolactone, combinations thereof, and the like, and Q can be a stiffening linkage such as a phthalic group, bisphenol A, biphenyl groups, diglycidyl ethers of bisphenol A, ethoxylated bisphenol A, terephthalic acid, phenylene diamine, toluene diamine, imides, and the like.

In embodiments $R_1$ and $R_2$ of the first polymer component may be polyalkylene oxides such as polyethylene oxides, typically polyethylene glycols (PEG). As used herein, polyethylene glycol generally refers to a polymer with a molecular weight of less than 50,000, while polyethylene oxide is used to refer to higher molecular weight polymers. The polymer backbone may be terminated with at least one amine group; in embodiments it may be terminated with two amine groups thus forming a diamine.

The preparation of amine-substituted polyalkylene oxides is within the purview of those skilled in the art. In fact, suitable amine-substituted polyalkylene oxides are commercially available from Shearwater Polymers, Inc., Huntsville, Ala.

The stiffening linkages included in the polymer backbone can include any groups that inhibit flexing of the polymer chain. Stiffening can be provided by either physical characteristics (steric hindrance) or chemical characteristics (charge repulsion) to inhibit flexing of the stiffening group. These stiffening linkages may provide the macromer composition of the present disclosure with additional strength necessary for certain medical applications, such as the adherence of pacemakers or closure of large surgical incisions, yet are compliant for use in vivo.

Methods for incorporating these stiffening linkages into the amine-terminated polyalkylene oxides are within the purview of those skilled in the art. In embodiments, the stiffening linkages may be incorporated by a ring-opening polymerization as follows:

such as sutures, for use with delicate or injured tissues without the mechanical stresses caused by the conventional tools.

The first polymer of the biocompatible synthetic macromer composition should have a molecular weight sufficiently high so that, when crosslinked with the second polymer component, the macromer composition provides adequate adhesive or sealant properties. At the same time, the molecular weight of the first polymer should be sufficiently low so that, upon degradation, the resulting polymer fragments can be excreted by the body. Thus, the molecular weight of the first polymer may be from about 1,000 to about 40,000, in embodiments from about 1,500 to about 10,000.

The first polymer component may be present in the biocompatible synthetic macromer composition of the present disclosure in amounts from about 10% to about 90% by weight of the macromer composition, in embodiments from about 15% to about 50% by weight of the macromer composition.

The second component of the biocompatible synthetic macromer composition of the present disclosure includes an amine-reactive group, such as a succinimidyl group or an isocyanate group. Suitable materials for use as the second component include polyalkylene oxides terminated with succinimidyl groups, isocyanate groups, or both, or diisocyanates such as ethylene diisocyanate, 1-6-hexamethylene diisocyanate (HMDI), 4,4'-oxybis(phenyl isocyanate),

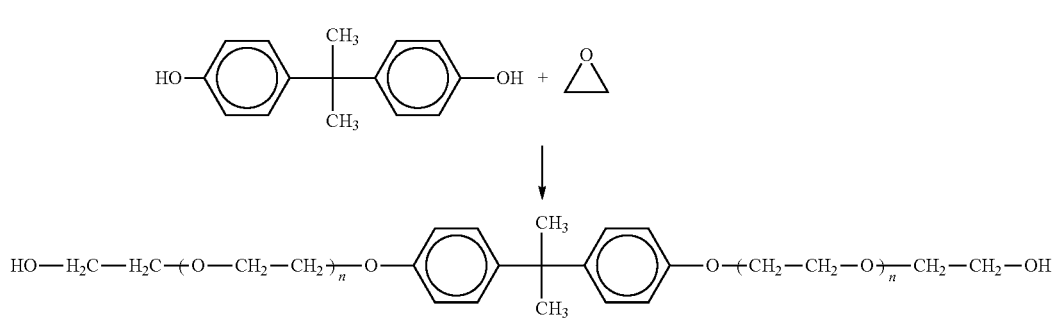

(II)

In other embodiments, the stiffening linkages may be incorporated by reacting terephthaloyl chloride with excess diamine functionalized PEG in the presence of triethylamine (Et$_3$N) following the general reaction scheme below:

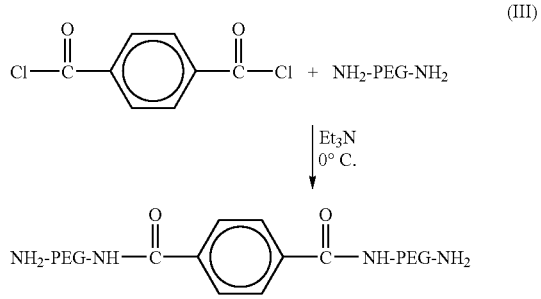

(III)

The strength added by the stiffening linkages of the present macromer adhesive composition distinguishes this composition from previously used surgical adhesives by providing the strength of conventional surgical closure tools, lysine diisocyanate, 2,4,6-trimethyl-1,3-phenylene diisocyanate, isophorone diisocyanate, cyclohexane-1,4-diisocyanate, 4,4'-dicyclohexylmethane diisocyanate, p-xylylene diisocyanate, tetramethylxylene diisocyanate, 1,4-phenylene diisocyanate, 2-4-toluene diisocyanate, 2,6-toluene diisocyanate, 4,4'-diphenylmethane diisocyanate, polymethylene polyphenyl polyisocyanates, 2,4'-diphenylmethane diisocyanate, 3(4)-isocyanatomethyl-1-methyl cyclohexyl isocyanate, 1,5-naphthylene diisocyanate, and mixtures and combinations thereof. A diisocyanate such as toluene diisocyanate, hexamethylene diisocyanate, methylene diphenyl diisocyanate, or an isocyanate-terminated polymer may be used as the second component in some embodiments. In other embodiments, the second component may be a polyalkylene oxide, such as a polyethylene glycol, with succinimidyl groups, isocyanate groups, or both.

In embodiments, the second component may be an isocyanate-terminated polyalkylene oxide, including a mixture of di-, tri-, and/or tetra-functional materials. In another embodiment, the second polymer can be a polyethylene oxide such as a PEG. The isocyanate groups and/or succinimidyl groups of the second component enhance the crosslinking of the first and second polymers to form a hydrogel.

In one embodiment, the second component corresponds to following formula (IV):

wherein n>1, typically from about 2 to about 4, X is a succinimidyl group, an isocyanate group, or both, and $R_3$ is a polyol such as sorbitol, mannitol, dextran, cyclodextrin, or a polyalkylene oxide, a polyethylene glycol with lactide linkages, or a poloxamer such as polyethylene oxide (PEO) copolymers with polypropylene oxide (PPO) such as the triblock PEO-PPO copolymers commercially available as PLURONICS® from BASF Corporation (Mt. Olive, N.J.).

In one embodiment, the second component can be of the formula:

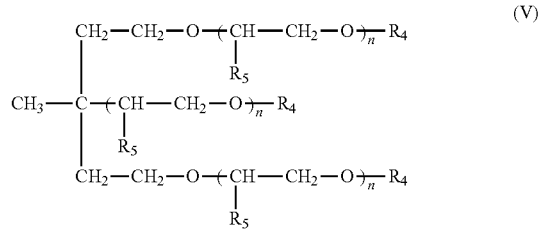

wherein n is a number from about 10 to about 250, $R_4$ is isocyanate or N-hydroxysuccinimide, and $R_5$ can be the same or different at each occurrence and is either hydrogren, a methyl group, or combinations thereof.

In some embodiments, the polyalkylene oxide of the second component may contain bioabsorbable groups such as esters, aliphatic esters, carbonates, orthoesters, phosphoesters, glycolic acid, glycolide, lactic acid, lactide, 1,4-dioxane-2-one, 1,3-dioxane-2-one, ε-caprolactone, and the like.

Where the second component is based upon a polyalkylene oxide, the amine-reactive groups, e.g. succinimidyl or isocyanate groups of the compounds of formula (IV) or formula (V) above, can be terminally located on the polyalkylene oxide arms or, alternatively, located at one or more location along the polyalkylene oxide arms. Likewise, although a single succinimidyl or isocyanate group per polyalkylene oxide arm may be present, it is also contemplated that more than one and up to ten or more succinimidyl or isocyanate groups per polyalkylene oxide arm may be present.

The second component of the composition of the present disclosure should have a molecular weight sufficiently high so that when crosslinked with the first polymer the macromer composition provides adequate adhesive and/or sealant properties. At the same time, the molecular weight of the second component should be sufficiently low so that upon degradation the resulting polymer fragments can be excreted by the body.

Where additional strength of the sealant is desired, the second component can also be stiffened and strengthened with a stiffening linkage. As described above, such linkages include phthalic, or biphenyl, or bisphenol A groups. In other embodiments, diglycidyl ethers of bisphenol A can be used as stiffening linkages. Other stiffening agents within the purview of those skilled in the art may be used. These groups can be incorporated into the second polymer before the first and second polymers are combined.

Methods for producing the amine-reactive polyalkylene oxides with stiffening linkages are within the purview of those skilled in the art. In embodiments, such polyalkylene oxides may be prepared by the following reaction scheme:

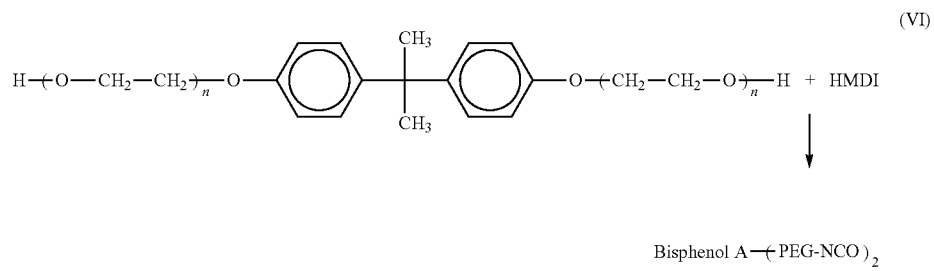

The second component may be present in the macromer composition of the present disclosure in amounts from about 90% to about 10% by weight of the macromer composition, in embodiments from about 85% to about 50% by weight of the macromer composition.

In some embodiments, the polyalkylene oxide backbone of the first polymer and/or second component can have a branched or multi-arm structure. For example, the polyalkylene oxide backbone can be the result of polymerizing an alkylene oxide monomer in the presence of a multi-functional (e.g., polyhydric) initiator. Reaction conditions for producing branched or multi-arm polyalkylene oxide backbones are within the purview of those skilled in the art.

The degree of substitution of the polymer will be a factor in the amount of crosslinking ultimately achieved and thus in the flexibility of the macromer composition of the present disclosure. The crosslinking between the first polymer and the second component can occur via hydrogen bonds and/or hydrophobic bonds. PEGs are commercially available from a variety of sources, including Nektar Therapeutics, 150 Industrial Road, San Carlos, Calif., USA 94070.

The selection of the components of the macromer compositions of the present disclosure can also be adjusted to tailor the macromer composition for optimal viscosity according the desired adhesive and/or sealant use. The viscosity of the macromer composition of the present disclosure should be sufficient to weld tissue yet still degrade in the body. Higher viscosities minimize displacement of the adhesive and/or sealant. Higher viscosities also improve the retention of uncured or unpolymerized adhesives and/or sealants at the site of application. These higher viscosities will, however, make the macromer compositions more difficult to apply. A useful viscosity for an adhesive and/or sealant utilizing a macromer composition of the present disclosure may be from about 200 centipoise ("cP") to about 100,000 cP, in embodiments from about 500 to about 10,000 cP.

Optionally, at least one additional component providing hydrolytically degradable bonds can be incorporated into the first polymer, the second component, or both, thereby increasing the rate at which the macromer composition of the present disclosure degrades. Suitable components which can be optionally incorporated include, but are not limited to, hydrolytically labile α-hydroxy acids (such as, for example, lactic or glycolic acid), lactones (such as, for example, ε-caprolactone), carbonates (such as, for example, trimethylene carbonate), ester ethers (such as, for example, dioxanones), diacids (such as, for example, succinnic acid, adipic acid, sebacic acid, malonic acid, glutaric acid, etc.), and combinations thereof. Those skilled in the art will readily envision reaction schemes for incorporating these components into the first polymer, the second component, or both.

For example, where the first polymer and second component are based on polyalkylene oxides, these hydrolytically degradable components can be incorporated into the first and/or second polyalkylene oxide by reacting both components with small amounts of diol. In embodiments a low weight PEG polymer may be combined with a diol mixture. The diol mixture results in degradable ester links between the highly branched polymer chains. A very low diol concentration should be used to prevent the polymer from gelling prematurely. The selected diol may be chosen according to the desired properties of the final sealant. For example, where mechanical enhancement is not desired or necessary, propylene fumarate, diethylene glycol or a short chain PEG diol can be used. Where additional strength of the sealant is desired, phthalic, biphenyl, bisphenol A, or a diglycidyl ether of bisphenol A groups can be used.

In addition to or in place of components that provide hydrolytically degradable linkages, at least one linkage that is enzymatically degradable may be incorporated into the first polymer, the second component, or both. Linkages which are enzymatically degradable include, but are not limited to: an amino acid residue such as -Arg-, -Ala-, -Ala(D)-, -Val-, -Leu-, -Lys-, -Pro-, -Phe-, -Tyr-, -Glu-, and the like; 2-mer to 6-mer oligopeptides such as -Ile-Glu-Gly-Arg-, -Ala-Gly-Pro-Arg-, -Arg-Val-(Arg)$_2$-, -Val-Pro-Arg-, -Gln-Ala-Arg-, -Gln-Gly-Arg-, -Asp-Pro-Arg-, -Gln(Arg)$_2$-, Phe-Arg-, -(Ala)$_3$-, -(Ala)$_2$-, -Ala-Ala(D)-, -(Ala)$_2$-Pro-Val-, -(Val)$_2$-, -(Ala)$_2$-Leu-, -Gly-Leu-, -Phe-Leu-, -Val-Leu-Lys-, -Gly-Pro-Leu-Gly-Pro-, -(Ala)$_2$-Phe-, -(Ala)$_2$-Tyr-, -(Ala)$_2$-His-, -(Ala)$_2$-Pro-Phe-, -Ala-Gly-Phe-, -Asp-Glu-, -(Glu)$_2$-, -Ala-Glu-, -Ile-Glu-, -Gly-Phe-Leu-Gly-, -(Arg)$_2$-; D-glucose, N-acetylgalactosamine, N-acetylneuraminic acid, N-acetylglucosamine, N-acetylmannnosamine or the oligosaccharides thereof; oligodeoxyribonucleic acids such as oligodeoxyadenine, oligodeoxyguanine, oligodeoxycytosine, and oligodeoxythymidine; oligoribonucleic acids such as oligoadenine, oligoguanine, oligocytosine, oligouridine, and the like. Those skilled in the art will readily envision reaction schemes for incorporating enzymatically degradable linkages into the polymer.

A variety of optional ingredients may be included in the macromer composition of the present disclosure. A phospholipid surfactant that provides antibacterial stabilizing properties and helps disperse other materials in the macromer composition of the present disclosure may be added. Optional additives include antimicrobial agents, colorants, preservatives, or medicinal agents such as, for example, protein and peptide preparations, antipyretic, antiphlogistic and analgesic agents, anti-inflammatory agents, vasodilators, antihypertensive and antiarrhythmic agents, hypotensive agents, antitussive agents, antineoplastics, local anesthetics, hormone preparations, antiasthmatic and antiallergic agents, antihistaminics, anticoagulants, antispasmodics, cerebral circulation and metabolism improvers, antidepressant and antianxiety agents, vitamin D preparations, hypoglycemic agents, antiulcer agents, hypnotics, antibiotics, antifungal agents, sedative agents, bronchodilator agents, antiviral agents and dysuric agents.

Additionally, an enzyme may be added to the macromer composition of the present disclosure to increase the rate of degradation of the macromer composition. Suitable enzymes include, for example, peptide hydrolases such as elastase, cathepsin G, cathepsin E, cathepsin B, cathepsin H, cathepsin L, trypsin, pepsin, chymotrypsin, γ-glutamyltransferase (γ-GTP) and the like; sugar chain hydrolases such as phosphorylase, neuraminidase, dextranase, amylase, lysozyme, oligosaccharase and the like; oligonucleotide hydrolases such as alkaline phosphatase, endoribonuclease, endodeoxyribonuclease, and the like. Enzymes may be added in lipsomes or microspheres to control their release and thus their effect on the degradation of the macromer composition of the present disclosure. Methods for incorporating enzymes into liposomes and microspheres are within the purview of those skilled in the art.

The macromer compositions of the present disclosure can be used in human and animal medical applications including, but not limited to, wound closure (including surgical incisions and other wounds), adhesives for medical devices (including implants), sealants and void fillers, and embolic agents.

In some embodiments, the first and second components are kept separate prior to application to tissue. Thus, the first and second components can be dispensed from a conventional two-part adhesive dispenser which provides mixing of the two components either prior to or after leaving the dispenser. Such dispensers are disclosed, for example, in U.S. Pat. Nos. 4,978,336, 4,361,055, 4,979,942, 4,359,049, 4,874,368, and 5,368,563, the disclosures of which are incorporated herein by reference.

Where the amine of the first component reacts with isocyanate of the second component, no water need be added; where the amine of the first component reacts with succinimidyl of the second component, water may be added.

In other embodiments, especially where the macromer composition of the present disclosure is to be utilized as a void filler or sealant to fill a defect in an animal's body, it may be advantageous to more precisely control the conditions and extent of cross-linking; in such a case, it may be useful to partially cross-link the macromer composition prior to its use to fill a void in animal tissue. In such a case the macromer composition of the present disclosure is applied to the void or defect and allowed to set, thereby filling the void or defect.

The macromer composition of the present disclosure can be used for a number of different applications. These applications include use as an adhesive to bind tissue together either as a replacement of, or as a supplement to, sutures, staples, tapes and/or bandages. Use of the disclosed macromer composition as an adhesive can eliminate or substantially reduce the number of sutures normally required during current practices, and eliminate the subsequent need for removal of staples and certain types of sutures. The use of macromer compositions of the present disclosure as an adhesive thus can be particularly useful with delicate tissues where sutures, clamps or other conventional tissue closure mechanisms may cause further tissue damage.

Additional applications for macromer compositions of the present disclosure include sealing tissues to prevent or control blood, or other fluid leaks, at suture or staple lines. In another embodiment, the macromer composition can be used to attach skin grafts and position tissue flaps during reconstructive surgery. In still another embodiment, the macromer composition can be used to close tissue flaps in periodontal surgery.

To effectuate the joining of two tissue edges, the two edges are approximated, and the first polymer with amine groups is combined with the second component with amine-reactive groups. The crosslinking reaction is rapid, generally taking less than one minute. Thus, the macromer composition of the present disclosure can be used as an adhesive to close a wound, including a surgical incision. In such a case, the macromer composition of the present disclosure can be applied to the wound and allowed to set, thereby closing the wound.

In embodiments, it may be useful to add a coupling agent to the first polymer, the second component, or both during formation of the macromer composition of the present disclosure. Suitable coupling agents are within the purview of those skilled in the art. In embodiments, a carbodiimide may be utilized as a coupling agent. Specific carbodiimides which may be utilized include, but are not limited to, 1-ethyl-3(3-dimethyl-aminopropyl)-carbodiimide hydrochloride.

In another embodiment, the present disclosure is directed to a method for using the macromer composition of the present disclosure to adhere a medical device to tissue, rather than secure two edges of tissue. In some embodiments, depending on the composition of the medical device, a coating having reactive groups to which the coupling agent can bind may be required on the medical device. In some cases such a coating can include the first polymer with amine groups, or the second component with amine-reactive groups. In some aspects, the medical device includes an implant. Other medical devices include, but are not limited to, pacemakers, stents, shunts and the like. Generally, for adhering a device to the surface of animal tissue, the macromer composition of the present disclosure, or components thereof, can be applied to the device, the tissue surface or both. The device, macromer composition and tissue surface are then brought into contact with each other and the composition is allowed to set, thereby adhering the device and surface to each other.

The macromer composition of the present disclosure can also be used to prevent post surgical adhesions. In such an application, the macromer composition is applied and cured as a layer on surfaces of internal tissues in order to prevent the formation of adhesions at a surgical site during the healing process.

When used as a sealant, the macromer composition of the present disclosure can be used in surgery to prevent or inhibit bleeding or fluid leakage both during and after a surgical procedure. It can also be applied to prevent air leaks associated with pulmonary surgery. The sealant may be applied directly to the desired area in at least an amount necessary to seal off any defect in the tissue and seal off any fluid or air movement.

Application of the macromer composition as an adhesive or sealant, with or without other additives, can be done by any conventional means. These include dripping, brushing, or other direct manipulation of the adhesive on the tissue surface, or spraying of the adhesive to the surface. In open surgery, application by hand, forceps or the like is contemplated. In endoscopic surgery, the adhesive can be delivered through the cannula of a trocar, and spread at the site by any device known in the art.

It will be understood that various modifications may be made to the embodiments disclosed herein. Therefore the above description should not be construed as limiting, but merely as exemplifications of preferred embodiments. Those skilled in the art will envision other modifications within the scope and spirit of the claims appended hereto.

What is claimed is:

1. A biocompatible synthetic macromer composition comprising a first polymer of formula $$H_2N-[R_1-Q-R_2]-NH_2 \qquad (I)$$

where $R_1$ and $R_2$ are the same or different and can be alkoxy or alkoxy with bioabsorbable groups, and Q is selected from the group consisting of bisphenol A, biphenyl, diglycidyl ethers of bisphenol A, ethoxylated bisphenol A, phenylene diamines, toluene diamine, and imides;

a second component having amine-reactive groups of the formula $$R_3(X)_n \qquad (IV)$$

wherein n>1, X is selected from the group consisting of succinimidyl groups, isocyanate groups, and combinations thereof, and $R_3$ is derived from a compound selected from the group consisting of sorbitol, mannitol, dextran, cyclodextrin, polyalkylene oxides, polyethylene glycols with lactide linkages, and polyethylene oxide copolymers with polypropylene oxide; and, a coupling agent,
wherein the composition has a viscosity from about 200 centipoise to about 100,000 centipoise.

2. A biocompatible synthetic macromer composition as in claim 1, wherein $R_1$ or $R_2$ is a polyethylene oxide.

3. A biocompatible synthetic macromer composition as in claim 1 wherein the bioabsorbable groups are derived from a compound selected from the group consisting of esters, aliphatic esters, carbonates, orthoesters, phosphoesters, glycolic acid, glycolide, lactic acid, lactide, 1,4-dioxane-2-one, 1,3-dioxane-2-one, ε-caprolactone, and combinations thereof.

4. A biocompatible synthetic macromer composition as in claim 1, wherein the first polymer is present in an amount from about 10% to about 90% by weight of the synthetic macromer composition.

5. A biocompatible synthetic macromer composition as in claim 1, wherein the second component is selected from the group consisting of di-functional polymers, tri-functional polymers, tetra-functional polymers, and mixtures thereof.

6. A biocompatible synthetic macromer composition as in claim 1, wherein the second component is a polyethylene glycol having multiple isocyanate groups.

7. A biocompatible synthetic macromer composition as in claim 1, wherein the second component is present in an amount from about 90% to about 10% by weight of the synthetic macromer composition.

8. A biocompatible synthetic macromer composition as in claim 1, wherein the first polymer is combined with hydrolytically degradable components.

9. A biocompatible synthetic macromer composition as in claim 1, wherein the first polymer is combined with enzymatically degradable components.

10. A biocompatible synthetic macromer composition as in claim 1, wherein the second component is combined with hydrolytically degradable components.

11. A biocompatible synthetic macromer composition as in claim 1, wherein the second component is combined with enzymatically degradable components.

12. A biocompatible synthetic macromer composition as in claim 1, wherein the coupling agent comprises a carbodiimide.

13. A biocompatible synthetic macromer composition as in claim 12, wherein the carbodiimide is 1-ethyl-3(3-dimethyl-aminopropyl)-carbodiimide hydrochloride.

14. An adhesive for wound closure comprising the biocompatible synthetic macromer composition of claim 1.

15. A sealant for use in a medical application comprising the biocompatible synthetic macromer composition of claim 1.

16. A biocompatible synthetic macromer composition as in claim 1, wherein the composition has a viscosity of from about 500 centipoise to about 10,000 centipoise.

* * * * *